United States Patent [19]

Goto et al.

[11] Patent Number: 4,855,076

[45] Date of Patent: Aug. 8, 1989

[54] FLUOROPHENYLCYCLOHEXANE DERIVATIVE

[75] Inventors: Yasuyuki Goto; Tetsuya Ogawa, both of Yokohama; Shigeru Sugimori, Musashino, all of Japan

[73] Assignee: Chisso Corporation, Japan

[21] Appl. No.: 907,092

[22] Filed: Sep. 15, 1986

[30] Foreign Application Priority Data

Sep. 17, 1985 [JP] Japan .................. 60-204666

[51] Int. Cl.$^4$ .................. C09K 19/30; C07C 69/76
[52] U.S. Cl. .................. 252/299.63; 560/102; 558/416
[58] Field of Search .................. 558/416; 560/102

[56] References Cited

U.S. PATENT DOCUMENTS

| | | | |
|---|---|---|---|
| 4,368,135 | 1/1983 | Osman | 252/299 |
| 4,387,038 | 6/1983 | Fukui et al. | 558/416 |
| 4,603,018 | 7/1986 | Sugimori et al. | 558/414 |

FOREIGN PATENT DOCUMENTS

| | | | |
|---|---|---|---|
| 19665 | 12/1980 | European Pat. Off. | 558/416 |
| 219975 | 4/1987 | European Pat. Off. | 560/102 |
| 148752 | 8/1984 | Japan | 558/416 |
| 59-148752 | 8/1984 | Japan | |

*Primary Examiner*—Anton H. Sutto
*Attorney, Agent, or Firm*—Leydig, Voit & Mayer

[57] ABSTRACT

A novel fluorophenylcyclohexane derivative useful as a component of liquid crystal compositions used for liquid crystal display elements, and a liquid crystal composition containing the same are provided, which fluorophenylcyclohexane derivative is expressed by the formula

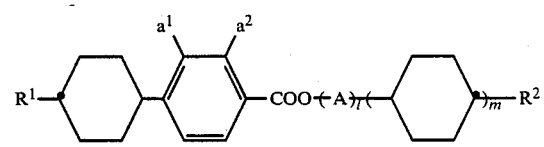

wherein $R^1$ represents an alkyl group of 1 to 10 carbon atoms; $R^2$ represents an alkyl group or an alkoxy group each of 1 to 10 carbon atoms; $a^1$ represents a hydrogen atom and $a^2$ represents a fluorine atom; A represents a 1,4-phenylene group; l and m each represent an integer of 0, 1 or 2 or 3; and a value of (l+m) is 2 or 3.

9 Claims, No Drawings

FLUOROPHENYLCYCLOHEXANE DERIVATIVE

BACKGROUND OF THE INVENTION

1. Field of the Invention

This invention relates to a fluorophenylcyclohexane derivative as a novel compound and a liquid crystal composition containing the derivative.

2. Description of the Related Art

Display elements utilizing the optical anisotropy and the dielectric anisotropy of liquid crystal compounds include those of various modes of twisted nematic (TN) type, dynamic scattering (DS) type, guest-host (GH) type, DAP type, etc., and the properties required for liquid crystal compounds vary depending on the respective modes, but it is a commone requirement that liquid crystal compounds exhibit liquid crystal phases within as broad a temperature range as possible and are stable to water, heat, light and air. At present, however, there is no single substance which satisfies all such requirements; thus it is the present status that liquid crystal compositions obtained by mixing several kinds of liquid crystal compounds or compounds similar to liquid crystals have been used.

SUMMARY OF THE INVENTION

The object of the present invention is to provide a novel compound useful as a component of a liquid crystal composition used for liquid crystal display elements, and also a novel liquid crystal composition containing the above liquid crystal compound.

The present invention in a first aspect resides in a fluorophenylcyclohexane derivative expressed by the formula

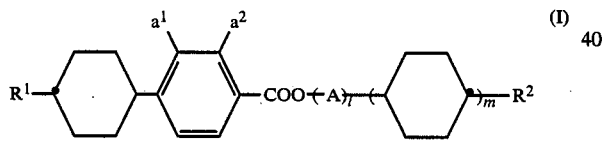

(I)

wherein $R^1$ represents an alkyl group of 1 to 10 carbon atoms; $R^2$ represents a hydrogen atom, or an alkyl group or an alkoxy group each of 1 to 10 carbon atoms, or a halogen atom of fluorine, chlorine or bromine or a cyano group; either one of $a^1$ or $a^2$ represents a fluorine atom and the other thereof represents a hydrogen atom; A represents a 1,4-phenylene group or a laterally substituted 1,4-phenylene group wherein a substituent is selected from the group consisting of fluorine and chlorine atoms and a cyano group; l and m each represent an integer of 0, 1, 2 or 3; and a value of (l+m) is 1 to 3.

The present invention in a second aspect resides in a liquid crystal composition comprising at least two components at least one of which is a fluorophenylcyclohexane derivative expressed by the above formula (I).

DETAILED DESCRIPTION OF PREFERRED EMBODIMENTS

The fluorophenylcyclohexane derivative expressed by the formula (I) includes the following compounds (a)~(y) preferred as component(s) of liquid crystal display materials:

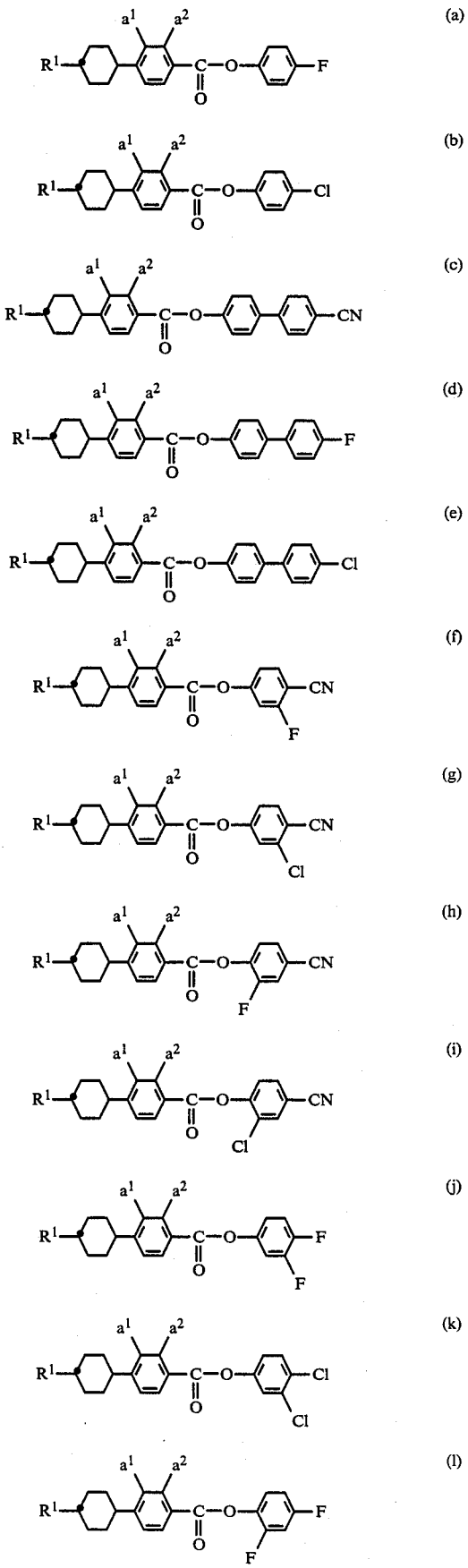

-continued (m) 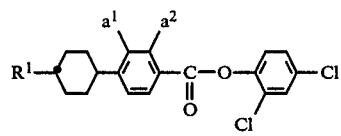

(n) 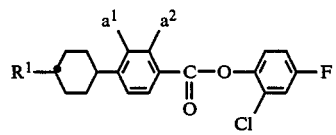

(o) 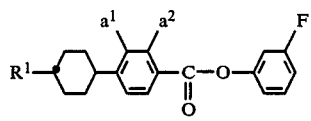

(p) 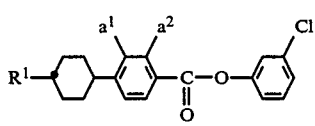

(q) 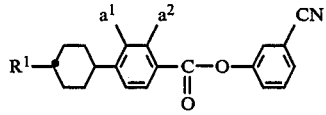

(r) 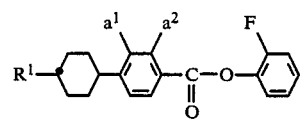

(s) 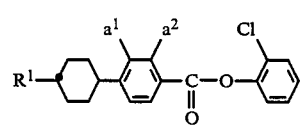

(t) 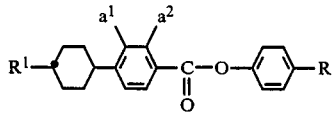

(u) 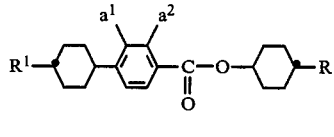

(v) 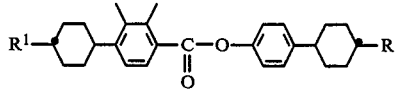

(w) 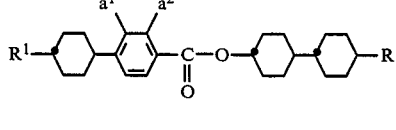

(x) 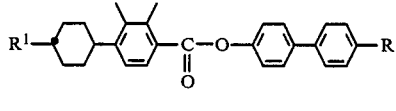

-continued (y) 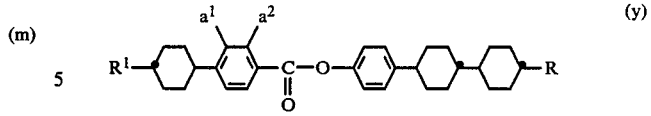

In these formulas, $a^1$, $a^2$ and $R^1$ are as defined above and R represents a hydrogen atom or an alkyl group or an alkoxy group each of 1 to 10 carbon atoms.

Among the compounds expressed by the formula (I), those having a linear chain alkyl group generally have a strong tendency to exhibit liquid crystal phases, while those having a branched alkyl group generally have a lower melting point than those having a linear chain group and a good compatability with other compounds.

According to the present invention, a F atom is introduced into the side position of the benzene ring in the substituted benzoic acid part of the compounds of the formula (I), the compounds having a lower melting point than compounds having no F atom introduced. Further, by the introduction of F atom, the compatibility of the compounds with other liquid crystal compounds is improved.

Among the compounds of the present invention, those of the above-illustrated formulas (a)~(y) have a broad mesomorphic range, and when such compounds are added as a component of liquid crystal compositions, it is possible to broaden the mesomorphic range of the compositions without raising the viscosity thereof so much. Further, since the compounds of the formulas (a)~(j) have a large positive dielectric anisotropy value, use of the compounds can increase the dielectric anisotropy value (hereinafter abbreviated to Δε) of liquid crystal compositions and also it is possible to operate liquid crystal display elements using the resulting liquid crystal compositions at a lower driving voltage.

Among the compounds expressed by the above formulas (k)~(s), there are many compounds having a medium extent of positive Δε values. These compounds are liquid crystal materials having a good compatibility with already existing liquid crystal substances and a relatively low viscosity.

Among the compounds expressed by the above formulas (t)~(y), there are many compounds having a negative Δε value. Among these liquid crystal compounds with negative dielectric anisotropy, there are many compounds having a broad mesomorphic range, a high clearing point, a much lower viscosity and a superior compatibility.

Next, an example of preparation of the compounds of the present invention will be described.

The compounds expressed by the formula (I) may be prepared according to a known method illustrated by the following reaction equation:

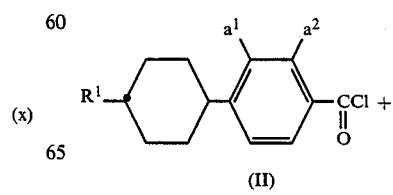

(II)

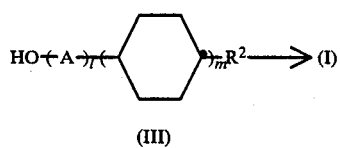

In the above equation, $R^1$, $R^2$, $a^1$, $a^2$, A, l and m are as defined above.

Namely, by reacting the corresponding benzoyl chloride (II) with the corresponding phenol derivative (III) or the corresponding cyclohexanol derivative (III) in the presence of pyridine, triethylamine or the like, it is possible to prepare the objective ester derivative (I).

The benzoyl chloride expressed by the formula (II) may be prepared for example according to the following method:

A cyclohexane derivative (VII) obtained by reducing a cylcohexene derivative (VI) while in turn obtained by a Grignard reaction of a 4-alkylcyclohexanone (IV) with a substituted bromobenzene derivative (V), is reacted with oxalic dichloride in the presence of aluminum chloride to obtain (II). These reactions are illustrated by the following reaction equations:

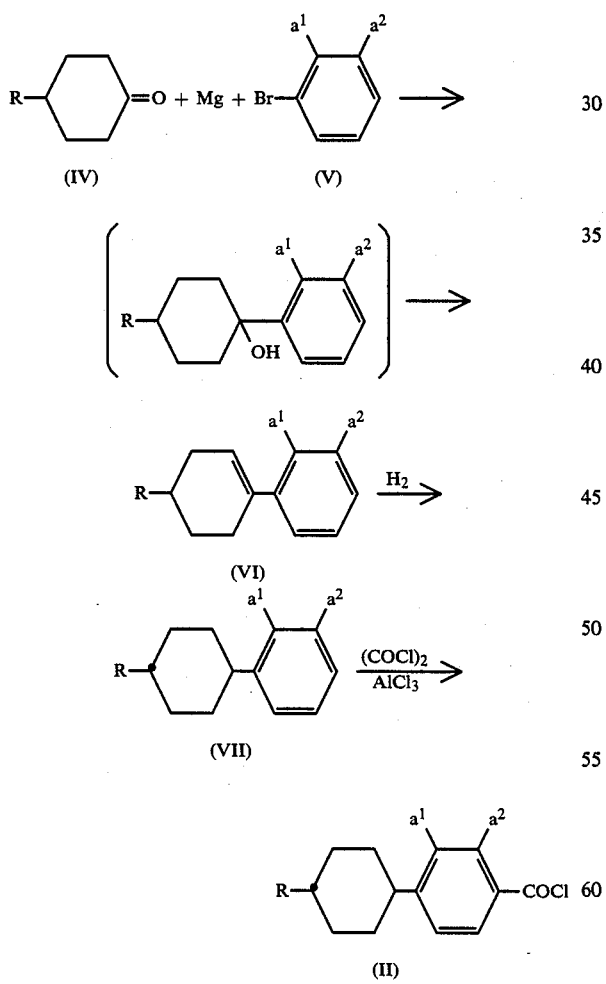

Further, the phenol derivative and the cyclohexanol derivative, expressed by the formulas (III), may be prepared according to a known method. Next, as to some of the compounds expressed by the formulas (a)~(y), preparation of the raw materials thereof will be illustrated. For example, preparations of the phenol or cyclohexanol derivatives (expressed by formulas (c'), (d'), etc., that is, those having prime attached to the corresponding formulas' symbols) as the raw materials for the compounds expressed by the formulas (c), (d), (e), (f), (v), (w), (x) and (y) are briefly described below.

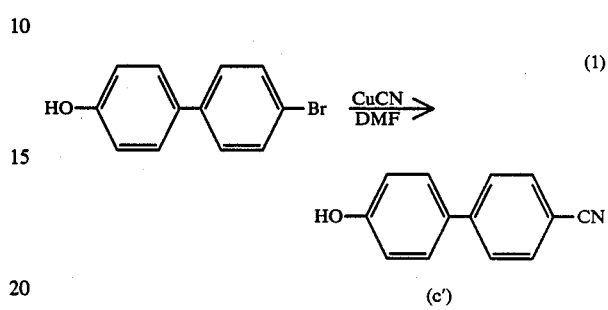

According to the method described in Japanese patent application laid-open No. Sho 57-64645/1982, phenol derivatives expressed by the formulas (d') and (e') are prepared.

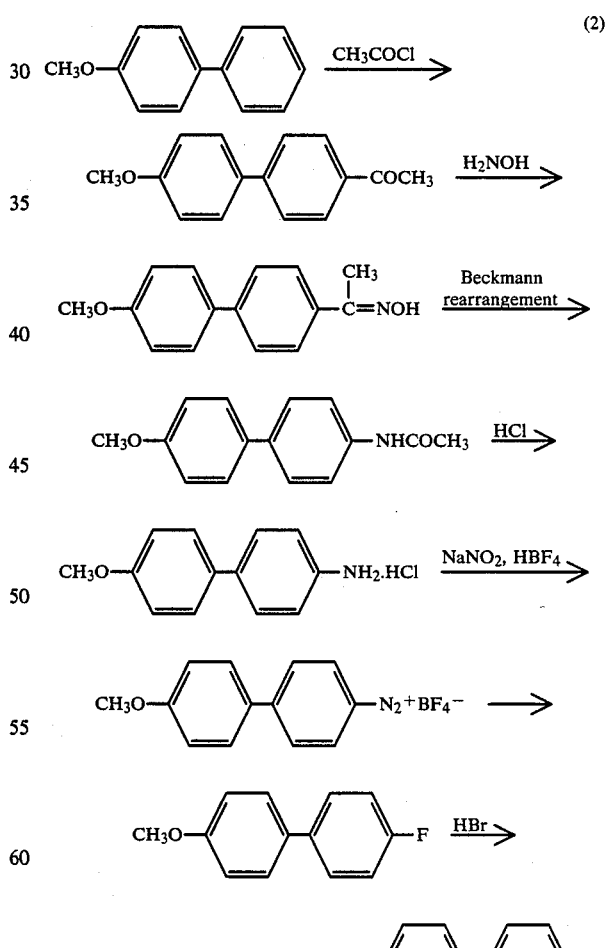

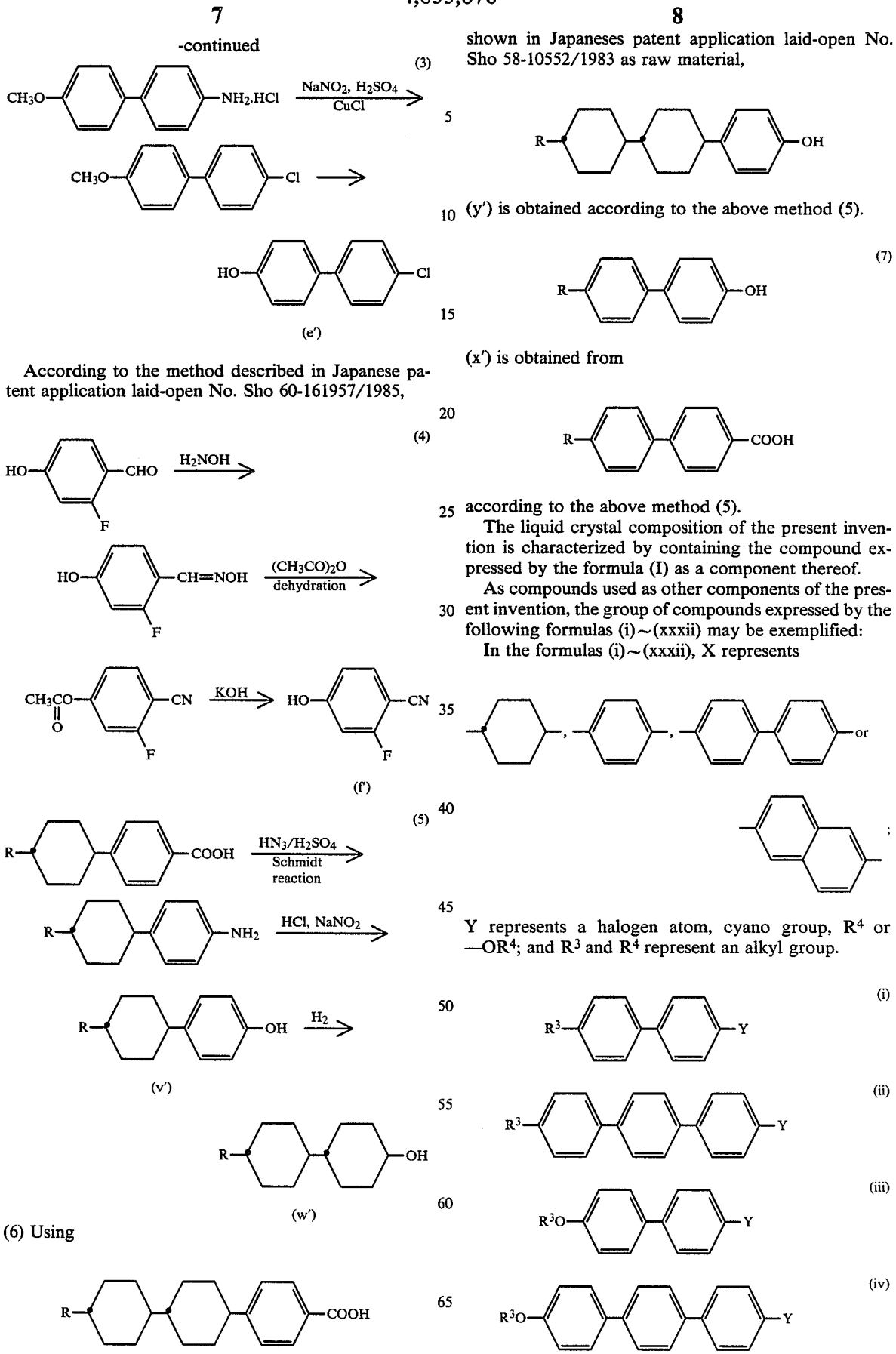

-continued

| | |
|---|---|
| R³—⟨cyclohexyl⟩—⟨phenyl⟩—Y | (v) |
| R³—⟨cyclohexyl⟩—⟨cyclohexyl⟩—⟨phenyl⟩—Y | (vi) |
| R³—⟨cyclohexyl⟩—⟨phenyl⟩—⟨phenyl⟩—Y | (vii) |
| R³—⟨phenyl⟩—COO—X—Y | (viii) |
| R³—⟨cyclohexyl⟩—COO—X—Y | (ix) |
| R³O—⟨phenyl⟩—COO—X—Y | (x) |
| R³—⟨phenyl⟩—N=N(O)—⟨phenyl⟩—Y | (xi) |
| R³O—⟨phenyl⟩—N=N(O)—⟨phenyl⟩—Y | (xii) |
| R³—⟨phenyl⟩—C≡C—⟨phenyl⟩—Y | (xiii) |
| R³O—⟨phenyl⟩—C≡C—⟨phenyl⟩—Y | (xiv) |
| R³—⟨phenyl⟩—CH=N—⟨phenyl⟩—Y | (xv) |
| R³O—⟨phenyl⟩—CH=N—⟨phenyl⟩—Y | (xvi) |
| R³—⟨bicyclo⟩—(⟨phenyl⟩)$_m$—Y  (m = 1,2) | (xvii) |

-continued

| | |
|---|---|
| R³—⟨phenyl⟩—⟨phenyl⟩—COO—X—Y | (xviii) |
| R³O—⟨phenyl⟩—⟨phenyl⟩—COO—X—Y | (xix) |
| R³—⟨bicyclo⟩—COO—X—Y | (xx) |
| R³—⟨cyclohexyl⟩—CH₂O—⟨phenyl⟩—Y | (xxi) |
| R³—⟨pyrimidinyl (N,N)⟩—⟨phenyl⟩—Y | (xxii) |
| R³—⟨pyrimidinyl (N,N)⟩—⟨phenyl⟩—X—Y | (xxiii) |
| R³—⟨bicyclo⟩—CH₂O—⟨phenyl⟩—Y | (xxiv) |
| R³—⟨dioxanyl⟩—⟨phenyl⟩—Y | (xxv) |
| R³—⟨dioxanyl⟩—⟨phenyl⟩—X—Y | (xxvi) |
| R³—⟨cyclohexyl⟩—⟨cyclohexyl⟩—Y | (xxvii) |
| R³—⟨cyclohexyl⟩—COO—⟨cyclohexyl⟩—Y | (xxviii) |
| R³—⟨cyclohexyl⟩—C₂H₄—⟨cyclohexyl⟩—Y | (xxix) |
| R³—⟨cyclohexyl⟩—C₂H₄—⟨cyclohexyl⟩—X—Y | (xxx) |

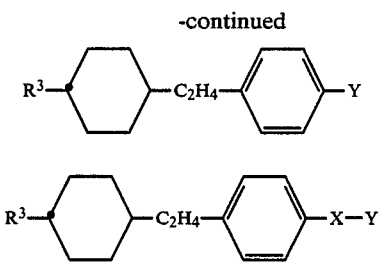

Among the liquid crystal compositions of the present invention, there are many compositions exhibiting a large positive dielectric anisotropy value, and these compositions are obtained by having 1 to 30% by weight of the compounds of the above formulas (a)~(j) contained therein.

In the case of these compositions, when the compounds of the present invention are added as a component thereof, the nematic phase temperature range is broadened toward the higher temperature side.

When the compounds of the present invention expressed by the formulas (t)~(y) are added to a nematic mixture having a negative $\Delta\epsilon$ value and composed mainly of compounds of the formulas (ix)~(xii) wherein X represents trans-1,4-cyclohexylene or 1,4-phenylene and Y represents an alkyl or alkoxy group, it is possible to obtain a liquid crystal mixture with negative dielectric anisotropy having a nematic range broadened toward the higher temperature side.

From the foregoing, it is seen that according to the present invention, the choice range of compounds usable as a component of useful liquid crystal compositions has been broadened very much.

The present invention will be described in more detail by way of Examples, but it should not be construed to be limited thereto.

In these Examples, the phase transition points are abbreviated as follows:

C-I point: crystalline-isotropic liquid phase transition point
C-N point: crystalline-nematic phase transition point
C-S point: crystalline-smectic phase transition point
S-N point: smectic-nematic phase transition point
N-I point: nematic-isotropic liquid phase transition point.

EXAMPLE 1

4-Fluorophenyl 2-fluoro-4-(trans-4-ethylcyclohexyl)benzoate

4-Fluorophenol (5.6 g, 0.05 mol) was dissolved in pyridine (10 ml), followed by adding to the solution, a solution of 2-fluoro-4-(trans-4-ethylcyclohexyl)benzoyl chloride (13.4 g, 0.05 mol) dissolved in toluene (50 ml), with stirring, thereafter heating the reaction mixture at 60° C. for 3 hours, adding water (100 ml) to the reaction material, washing the separated toluene layer with 6N HCl, then with 2N NaOH aqueous solution and further with water, thereafter drying it with anhydrous sodium sulfate, distilling off toluene and recrystallizing the residual solids from ethyl acetate to obtain the objective 4-fluorophenyl 2-fluoro-4-(trans-4-ethylcyclohexyl)benzoate (12.2 g, yield 65%). This compound exhibited following phase transition points:

C-N point: 65.6° C., N-I point: 113.2° C.

EXAMPLES 2-27

The following compounds were obtained according to the method of Example 1:

(Example 2)
4-Chlorophenyl 2-fluoro-4-(trans-4-ethylcyclohexyl)benzoate
C-N point: 73.5° C., N-I point: 148.9° C.

(Example 3)
4'-Fluorobiphenyl-4-yl 2-fluoro-4-(trans-4-ethylcyclohexyl)benzoate
C-N point: 98.6° C., N-I point: 288.0° C.

(Example 4)
4'-Cyanobiphenyl-4-yl 2-fluoro-4-(trans-4-ethylcyclohexyl)benzoate
C-N point: 131.7° C., N-I point: higher than 300° C.

(Example 5)
2-Fluorophenyl 2-fluoro-4-(trans-4-ethylcyclohexyl)benzoate
C-I point: 61.8° C., N-I point: 20.8° C.

(Example 6)
2-Chlorophenyl 2-fluoro-4-(trans-4-ethylcyclohexyl)benzoate
C-I point: 95.0° C.

(Example 7)
3-Fluorophenyl 2-fluoro-4-(trans-4-ethylcyclohexyl)benzoate
C-I point: 47.6° C., N-I point: 31.6° C.

(Example 8)
3-Chlorophenyl 2-fluoro-4-(trans-4-ethylcyclohexyl)benzoate
C-I point: 64.6° C.

(Example 9)
3-Cyanophenyl 2-fluoro-4-(trans-4-ethylcyclohexyl)benzoate
C-I point: 69.9° C.

(Example 10)
2,4-Difluorophenyl 2-fluoro-4-(trans-ethylcyclohexyl)benzoate
C-N point: 62.5° C., N-I point: 82.3° C.

(Example 11)
2-Chloro-4-fluorophenyl 2-fluoro-4-(trans-4-ethylcyclohexyl)benzoate
C-I point: 59.3° C., N-I point: 32.5° C.

(Example 12)
2,4-Dichlorophenyl 2-fluoro-4-trans-4-ethylcyclohexyl)benzoate
C-I point: 68.2° C., N-I point: 66.1° C.

(Example 13)
3-Chloro-4-fluorophenyl 2-fluoro-4-(trans-4-ethylcyclohexyl)benzoate
C-I point: 56.9° C., N-I point: 2.0° C.

(Example 14)
3,4-Dichlorophenyl 2-fluoro-4-(trans-4-ethylcyclohexyl)benzoate
C-I point: 58.8° C., N-I point: 45.1° C.

(Example 15)
2,6-Difluorophenyl 2-fluoro-4-(trans-4-ethylcyclohexyl)benzoate
C-I point: 81.3° C.

(Example 16)
2,3,5,6-Tetrafluorophenyl 2-fluoro-4-(trans-4-ethylcyclohexyl)benzoate
C-I point: 76.6° C.

(Example 17)
2,3,4,5,6-Pentafluorophenyl 2-fluoro-4-(trans-4-ethylcyclohexyl)benzoate
C-I point: 67.2° C., N-I point: 21.6° C.

(Example 18)
3-Fluoro-4-cyanophenyl 2-fluoro-4-(trans-4-ethylcyclohexyl)benzoate
C-N point: 60.9° C., N-I point: 160.5° C.
(Example 19)
3-Chloro-4-cyanophenyl 2-fluoro-4-(trans-4-ethylcyclohexyl)benzoate
C-N point: 74.5° C., N-I point: 94.6° C.
(Example 20)
2-Fluoro-4-cyanophenyl 2-fluoro-4-(trans-4-ethylcyclohexyl)benzoate
C-N point: 127.7° C., N-I point: 185.7° C.
(Example 21)
Phenyl 2-fluoro-4-(trans-4-ethylcyclohexyl)benzoate
C-I point: 60.4° C., N-I point: 50.2° C.
(Example 22)
4-Pentylphenyl 2-fluoro-4-(trans-4-ethylcyclohexyl)benzoate
C-N point: 49.5° C., N-I point: 135.6° C.
(Example 23)
4-Propoxyphenyl 2-fluoro-4-(trans-4-ethylcyclohexyl)benzoate
C-N point: 77.4° C., N-I point: 168.2° C.
(Example 24)
4-(Trans-4-propylcyclohexyl)phenyl 2-fluoro-4-(trans-4-ethylcyclohexyl)benzoate
C-N point: 140.5° C., N-I point: 293° C.
(Example 25)
4-(Trans, trans4'-propylbicyclohexyl-4-yl)phenyl 2-fluoro-4-(trans-4-ethylcyclohexyl)benzoate
C-S point: 162.0° C., S-N point: 163.8° C., N-I point: 300.0° C.
(Example 26)
Trans-4-pentylcyclohexyl 2-fluoro-4-(trans-4-ethylcyclohexyl)benzoate
C-N point: 63.4° C., N-I point: 122.1° C.
(Example 27)
Trans-4-(trans-4-propylcyclohexyl)cyclohexyl 2-fluoro-4-(trans-4-ethylcyclohexyl)benzoate
C-N point: 84.8° C., N-I point: 253.5° C.

EXAMPLE 28

A liquid crystal mixture (A) consisting of

| (A) | trans-4-propyl-(4-cyanophenyl)cyclohexane 30% by weight, trans-4-pentyl-(4-cyanophenyl)cyclohexane 40% by weight and trans-4-heptyl-(4-cyanophenyl)cyclohexane 30% by weight |
|---|---| has a N-I point of 52.1° C., a Δε value of +11.2 and a viscosity at 20° C. of 23.4 cp. This mixture was sealed in a TN type cell of 10 μm thick and its characteristics at 20° C. were measured to give a threshold voltage of 1.54 V and a saturation voltage of 2.13 V.

In 85% by weight of this liquid crystal mixture (A) was dissolved 15% by weight of 4-fluorophenyl 2-fluoro-4-(trans-4-ethylcyclohexyl)benzoate. The resulting composition had a N-I point of 54.1° C., a Δε value of +12.8 and a viscosity at 20° C. of 25.0 cp. This liquid crystal composition was sealed in the above TN cell and its characteristics at 20° C. were measured. As a result, the threshold voltage and saturation voltage lowered down to 1.44 V and 1.65 V, respectively.

EXAMPLE 29

A liquid crystal mixture consisting of

| trans-4-propyl-(4-cyanophenyl)cyclohexane 25.5% by weight, trans-4-pentyl-(4-cyanophenyl)cyclohexane 34% by weight, trans-4-heptyl-(4-cyanophenyl)cyclohexane 25.5% by weight and 4'-fluoro-4-biphenyl-4-yl 2-fluoro-4-(trans-4-ethylcyclohexyl)benzoate 15.0% by weight |
|---| had a N-I point of 71.9° C., a Δε value of 11.7 and a viscosity at 20° C. of 29.0 cp.

Further, this liquid crystal mixture was sealed in the same cell as used in Example 28. The resulting TN cell had a threshold voltage of 1.60 V and a saturation voltage of 2.24 V.

EXAMPLE 30

A liquid crystal mixture consisting of

| trans-4-propyl-(4-cyanophenyl)cyclohexane 25.5% by weight, trans-4-pentyl-(4-cyanophenyl)cyclohexane 34% by weight, trans-4-heptyl-(4-cyanophenyl)cyclohexane 25.5% by weight and 3-fluoro-4-cyanophenyl 2-fluoro-4-(trans-4-ethylcyclohexyl)benzoate 15.0% by weight |
|---| had a N-I point of 59.3° C., a Δε value of 15.3 and a viscosity at 20° C. of 30.3 cp. Further, a TN cell prepared in the same manner as in Example 28 with the composition had a threshold voltage of 1.35 V and a saturation voltage of 1.89 V.

EXAMPLE 31

A liquid crystal mixture consisting of

| trans-4-propyl-(4-cyanophenyl)cyclohexane 25.5% by weight, trans-4-pentyl-(4-cyanophenyl)cyclohexane 34% by weight, trans-4-heptyl-(4-cyanophenyl)cyclohexane 25.5% by weight and 4-(trans-4-propylcyclohexyl)phenyl 2-fluoro-4-(trans-4-ethylcyclohexyl)benzoate 15.0% by weight |
|---| had a N-I point of 77.7° C., a Δε value of 10.9 and a viscosity at 20° C. of 28.4 cp. Further, a TN cell prepared in the same manner as in Example 28 with the composition had a threshold voltage of 1.74 V and a saturation voltage of 2.40 V.

What we claim is:

1. A fluorophenylcyclohexane derivative and expressed by the formula $$R^1-\bigcirc-\bigcirc-COO-(\bigcirc)_l-(\bigcirc)_m-R$$

wherein R represents an alkyl or alkoxy group of 1-10 carbon atoms; $R^1$ represents an alkyl group of 1-10 carbon atoms; l and m each represent integers of 0 to 2; and a value of (l+m) is 2 or 3.

2. A fluorophenycyclohexane derivative according to claim 1 wherein l is 0 and m is 2.

3. A fluorophenylcyclohexane derivative according to claim 1 wherein l is 1 and m is 1.

4. A fluorophenylcyclohexane derivative according to claim 1 wherein l is 1 and m is 2.

5. A fluorophenylcyclohexane derivative according to claim 1 wherein $R^1$ is ethyl.

6. A fluorophenylcyclohexane derivative according to claim 1 wherein R is propyl.

7. A fluorophenylcyclohexane derivative according to claim 1 wherein R is pentyl.

8. A fluorophenylcyclohexane derivative according to claim 1 wherein R is propoxyl.

9. A liquid crystal composition comprising at least two components, at least one of which is a fluorophenylcyclohexane derivative as defined in claim 1.

* * * * *